(12) United States Patent
Gammons

(10) Patent No.: US 6,994,720 B2
(45) Date of Patent: Feb. 7, 2006

(54) INFLATABLE THERMAL BLANKET WITH STERILE ACCESS

(75) Inventor: Clifford E. Gammons, Loudon, TN (US)

(73) Assignee: Adroit Development, Inc., Loudon, TN (US)

(*) Notice: Subject to any disclaimer, the term of this patent is extended or adjusted under 35 U.S.C. 154(b) by 31 days.

(21) Appl. No.: 10/727,859

(22) Filed: Dec. 4, 2003

(65) Prior Publication Data
US 2005/0125047 A1 Jun. 9, 2005

(51) Int. Cl.
*A61F 7/00* (2006.01)

(52) U.S. Cl. .................................... 607/104; 607/114
(58) Field of Classification Search ............... 607/96, 607/104, 108–112, 114
See application file for complete search history.

(56) References Cited

U.S. PATENT DOCUMENTS

| 5,184,612 | A | 2/1993 | Augustine |
| 5,304,213 | A | 4/1994 | Berke et al. |
| 5,324,320 | A | 6/1994 | Augustine et al. |
| 5,405,370 | A * | 4/1995 | Irani ........................ 607/104 |
| 5,443,488 | A | 8/1995 | Namenye et al. |
| 5,674,269 | A | 10/1997 | Augustine |
| 5,989,285 | A | 11/1999 | DeVilbiss et al. .......... 607/107 |
| 6,176,870 | B1 * | 1/2001 | Augustine .................. 607/107 |
| 6,203,567 | B1 * | 3/2001 | Augustine .................. 604/104 |

* cited by examiner

*Primary Examiner*—Roy D. Gibson
(74) *Attorney, Agent, or Firm*—Pitts & Brittian, P.C.

(57) ABSTRACT

An apparatus for pneumatic therapy blanket with sterile access. In one embodiment, an inflatable therapy blanket, which is sterilized, has an opening in the patient's chest area. In another embodiment, a perforated seam is positioned along the longitudinal axis of the blanket between the patient's neck and the access opening. By breaking the perforation, a slit is formed, allowing access to the patient's body from outside the blanket. In another embodiment, the blanket covers only the lower portion of the patient's body and the blanket has a tape edge for attaching the blanket to the patient's body.

19 Claims, 3 Drawing Sheets

INFLATABLE THERMAL BLANKET WITH STERILE ACCESS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention relates to a blanket for covering at least a portion of the body of a human, or other animal, in order to bath the body portion in a conditioned gas. More specifically, the present invention is related to an inflatable thermal blanket having air flow channels for directing a conditioned gas, such as, for example, heated air, to a selected portion of the body of a user while allowing a medical person to access a portion of the body with sterile access.

2. Description of the Related Art

Inflatable thermal blankets which are used to communicate a conditioned gas, such as heated or cooled air, to a patient are known in the art. Such thermal blankets typically have an inflatable portion provided with an inlet port for placing the inflatable portion in fluid communication with a source of pressurized, conditioned gas such that the inflatable portion can be selectively inflated. The inflatable portion generally has an inner surface which is gas pervious, or which is otherwise adapted to communicate the conditioned gas used to inflate the blanket to the user. Such thermal blankets are often used to treat conditions such as hypothermia, or used to reduce the body temperature of a user in circumstances where the body temperature is inappropriately high. For example, where a patient is being treated for hypothermia, at least a portion of the patient's body is covered with the thermal blanket, and warm air is pumped into the inflatable portion. The warm air used to inflate the inflatable portion is thereafter communicated through the inner surface of the inflatable portion so as to bath the body portion covered by the blanket in warm air. Examples of such thermal blankets are disclosed in U.S. Pat. Nos. 5,184,612; 5,304,213; and 5,324,320.

Whereas prior art thermal blankets serve to deliver conditioned air to a patient, the temperature of the air being communicated through the inner surface of the inflatable portion, and the surface temperature of the inner surface, can vary greatly over the area of the inner surface. For example, if heated air is pumped into the inflatable portion through the inlet port, the air within the blanket near the inlet port tends to be substantially higher in temperature than the air within the blanket which is remote from the inlet port. Accordingly, the inner surface of the blanket proximate the inlet port, and the air communicated to the patient through the inner surface of the blanket proximate the inlet port, can be uncomfortably, or damagingly, hot when the blanket is otherwise communicating air of the desired temperature to the patient. Whereas the temperature of the air entering the inlet port can be reduced to avoid uncomfortable, or damaging, hot spots near the inlet port, such a reduction of temperature can compromise the overall effectiveness of the thermal blanket.

U.S. Pat. No. 5,443,488, titled "Thermal Blanket with Surgical Access," issued to Namenye, et al., on Aug. 22, 1995, discloses "a disposable pneumatic thermal blanket for controlling a patient's body temperature wherein the blanket includes structure for providing access through the blanket for surgical purposes." The '488 patent discloses an access opening 74 through the blanket 10 formed by a plurality of perforated slits 26, 28, 30, 34, 38 extending through the blanket 10. The perforations initially hold the shape of the blanket 10 during shipping and handling and weaken the blanket 10 so that the desired access opening 74 is formed by pulling the blanket 10 apart upon opposite sides of the slits 26, 28, 30, 34, 38. The excess blanket material or flaps 68 are rolled to form rolls 72, which expose a portion of the body under the blanket 10.

U.S. Pat. No. 5,674,269, titled "Patient Warming System with User-Configurable Access Panel," issued to Augustine on Oct. 7, 1997, discloses a U-shaped pneumatic thermal device 100 for controlling a patient's body temperature and a deformally resilient, insulating access panel 118 between the tube legs 110, 112 of the thermal device 100. The access panel 118 has pliable, opposing fingers 200, 201, which are pulled away from the patient 104 to provide access. The panel 118 has pliable, opposing fingers 206, 207, which are tucked between the patient 104 and the device 100 to provide access. The fingers 200 to 207 are created by tearing perforations between the fingers to be separated from the panel 118.

BRIEF SUMMARY OF THE INVENTION

According to one embodiment of the present invention, a full body pneumatic therapy blanket with sterile access is provided. The therapy blanket covers the body of a patient and has an access opening formed in the area of the blanket that covers the chest of the patient. Another embodiment of the therapy blanket has a perforated slit in the area between the access opening and the patient's neck. Still another embodiment provides a blanket that covers the lower half of the patient, with a taped connection securing the blanket to the patient.

The thermal blanket includes an inflatable portion for receiving the conditioned gas under pressure and for being positioned over at least a portion of the body of the user. The inflatable portion is defined by a base sheet which is fabricated of a gas pervious material, or which is otherwise adapted for communicating the conditioned gas to a portion of the body, and by an outer sheet which is substantially gas impervious. The inflatable portion also includes an inlet port for placing the inflatable portion in fluid communication with a source of conditioned gas. The inflatable portion is constructed so as to direct the conditioned gas along defined paths inside the inflatable portion. The defined paths are channels formed by joining the base sheet and outer sheet. Another embodiment provides an inflatable portion that also includes a barrier sheet that is positioned adjacent the base sheet and which prevents the conditioned gas from passing through that portion of the base sheet so protected.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
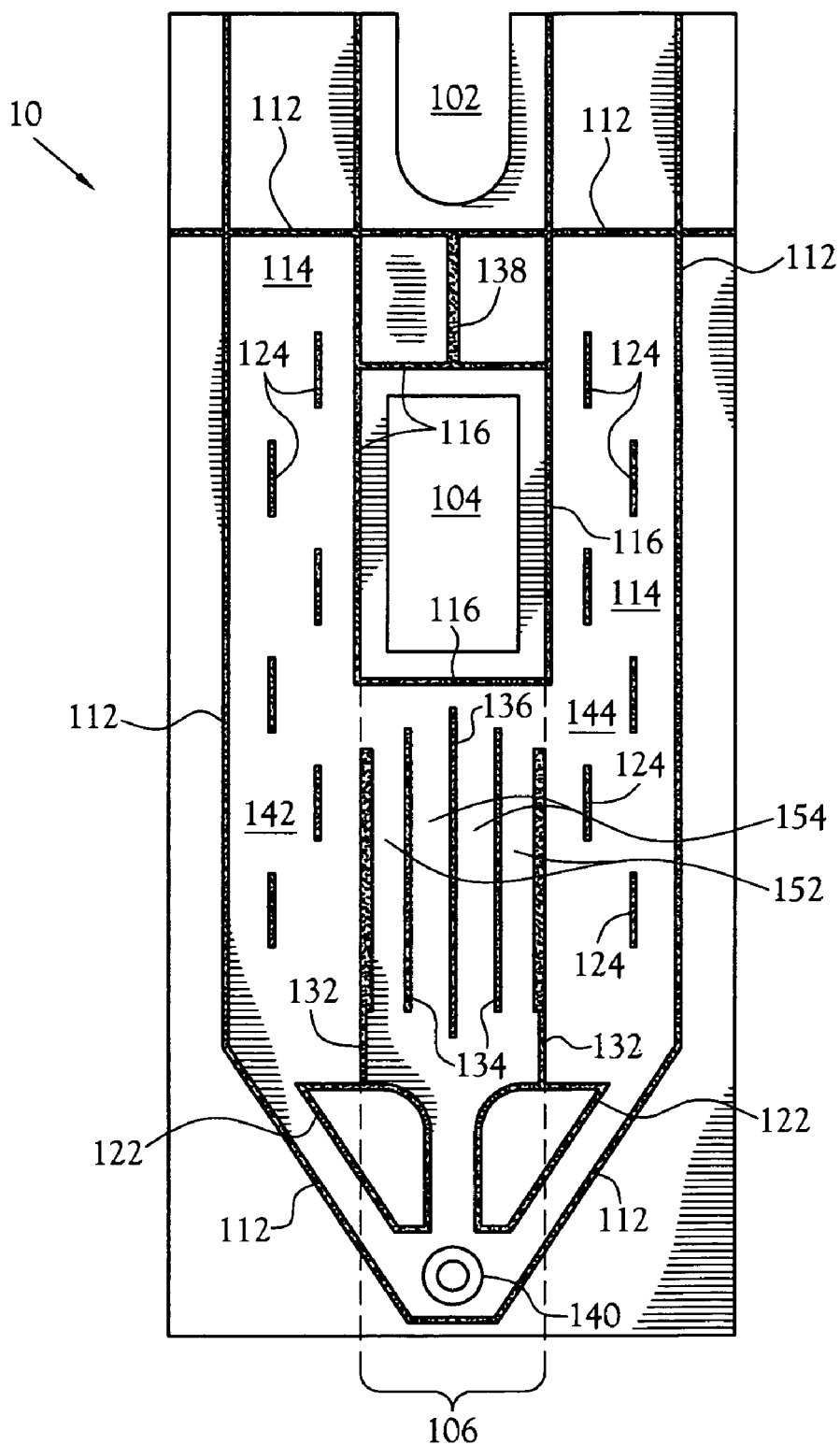
FIG. 1 is a plan view of one embodiment of a therapy blanket.
Figure 2:
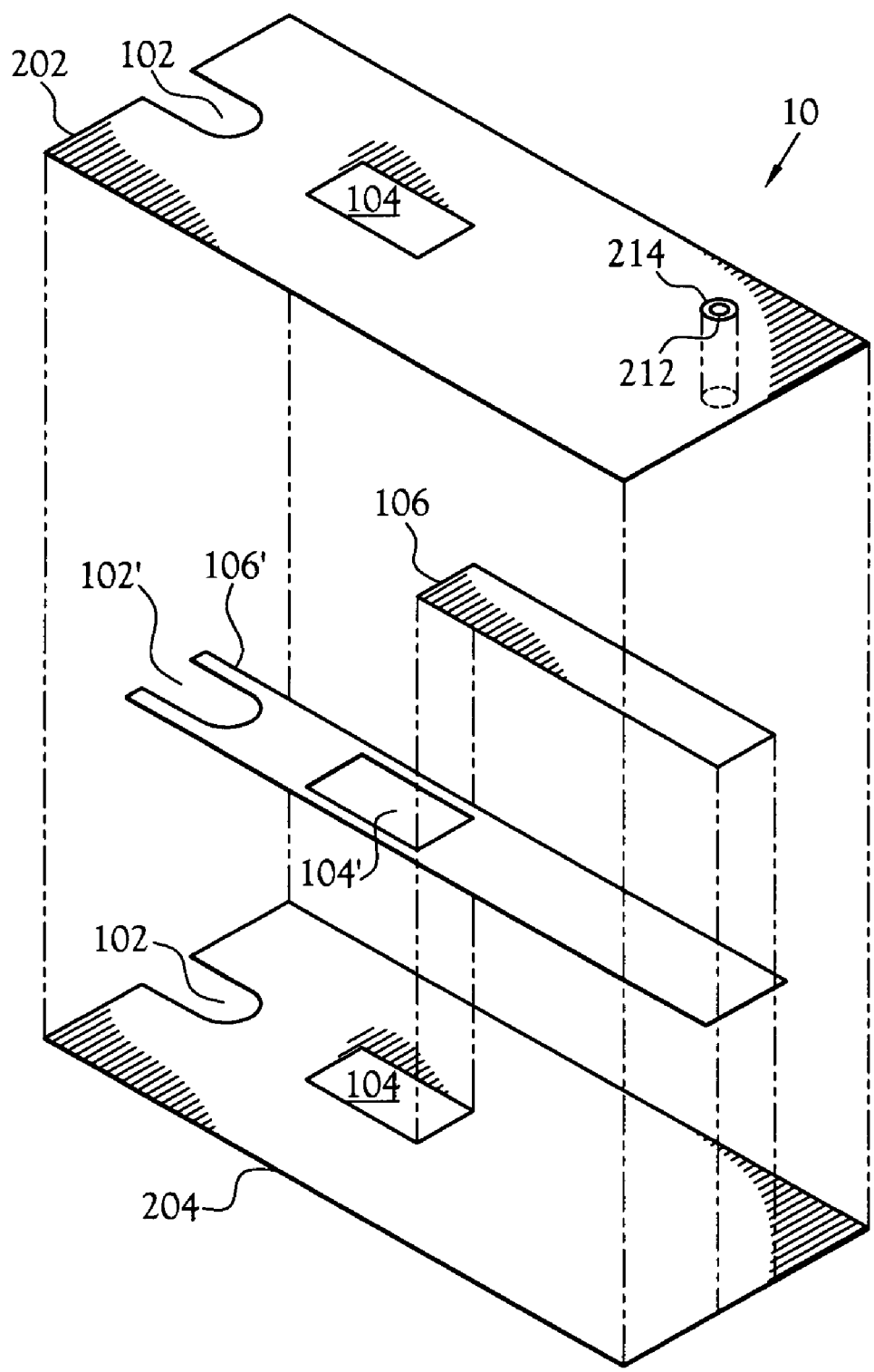
FIG. 2 is an exploded, perspective view of the therapy blanket.
Figure 3:
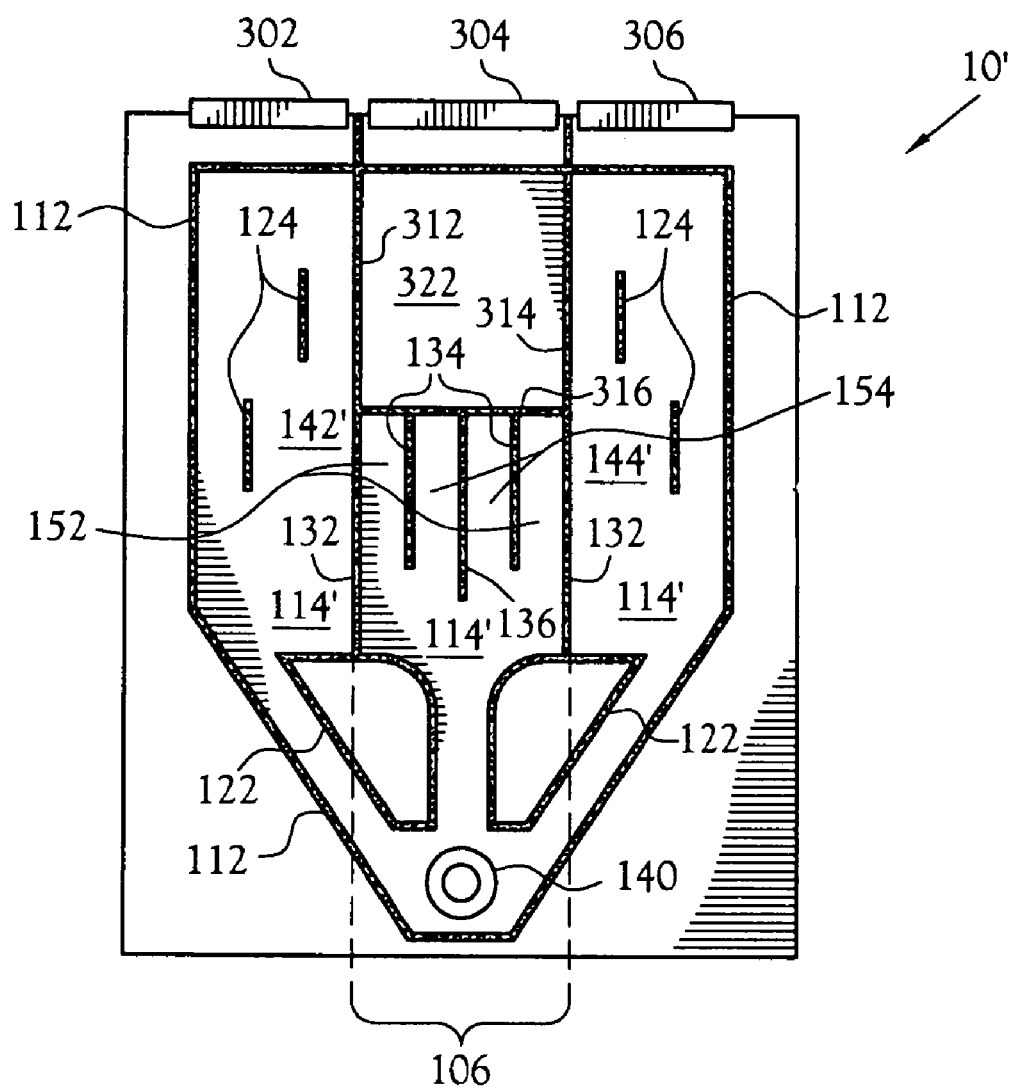
FIG. 3 is a plan view of another embodiment of a therapy blanket.

An inflatable thermal blanket in accordance with the present invention is illustrated generally at 10 in FIGS. 1 and 2 and generally at 10' in FIG. 3. The thermal blanket 10, 10' is designed to cover at least a portion of the body of a human, or other animal, and to bath at least a portion of such body with a conditioned gas, such as thermally conditioned air. The thermal blanket 10, 10' is particularly useful in bathing a body portion in air which has been heated to a temperature above normal body temperature in order to treat conditions such as hypothermia. However, it will be understood that gaseous fluids other than air can be used, and in certain applications the gaseous fluid utilized may be delivered to the body portion at a temperature which is at, or lower than, normal body temperature, as in the case where the existing body temperature is abnormally high and cooling is desired. The thermal blanket 10, 10' is suitable for sterilization and use in a sterile environment.

FIG. 1 illustrates a thermal blanket 10 for covering the full body of a patient. The blanket 10 is rectangular and includes an inflatable portion 114 surrounded by a seam 112, which joins the sheets 202, 204 forming the blanket 10. The blanket 10 extends beyond the inflatable portion 114 so as to drape over the patient in order to help retain the conditioned gas communicated to the patient. About where the patient's chest would be located under the blanket 10 is an access opening 104. The access opening 104 is smaller than the area bounded by seam 116, which forms one boundary of the inflatable portion 114. The edges of the access opening 104, in one embodiment, are taped to the patient to provide sterile access to a portion of the patient's body. Taping the edges of the access opening 104 prevents the air escaping from the blanket 10 from entering the access opening 104.

In the illustrated embodiment, the blanket 10 is designed to accommodate the neck of a patient in slot 102. The inlet port 140, located near the feet of the patient, is available for connecting a blower for inflating the blanket 10.

The inflatable portion 114 is defined by the seam 112, which contains the inflatable portion 114 near the outside edge of the blanket 10, and by the seam 116 around the edge of the opening 104. Inside the inflatable portion 114 are air flow channels 142, 144, 152, 154 formed by other seams 132, 134, 136. A pair of air flow channels 142, 144 extending the length of the inflatable portion 114 are defined by seams 112, 116, 132. This pair of air flow channels 142, 144 has a series of alternating seals 124, which serve to prevent the channels 142, 144 from inflating to a large cylindrical shape. A group of parallel inside channels 152, 154 are defined by seams 132, 134, 136. These channels 152, 154 serve to flatten the blanket 10 across the legs of the patient. Because of the barrier sheet 106, the conditioned air does not exhaust through the inside channels 152, 154.

The seams 122 define two un-inflated regions in the inflatable portion 114. The un-inflated regions serve to direct the air from the inlet port 140 into the various air flow channels 142, 144, 152, 154 by dividing the inflatable portion 114 near the inlet port 140 into three channels. Those skilled in the art will recognize that, by varying the placement of the seams 122, the amount of air flowing into the channels 142, 144, 152, 154 can be controlled.

In one embodiment, seam 138 is a double wide seam with perforations aligned along the centerline of the seam 138. By pulling the fabric of the blanket 10 away from the seam 138, the perforations separate and a slit is formed in the blanket 10 where the seam 138 is located. This slit provides an opening for routing catheters, tubes, wires, and other items to the patient in the area of the patient's neck and upper chest. Those skilled in the art will recognize that the width of each of the perforated seams can be varied to provide the necessary strength after the seam is perforated and that the seam can be a single-width seam without departing from the spirit and scope of the present invention.

In another embodiment, the seams 152, 154 are double wide seams with perforations aligned along the centerline of the seams 152, 154. By pulling the fabric of the blanket 10 away from the seams 152, 154, the perforations separate and slits are formed in the blanket 10 where the seams 152, 154 are located. These slits provide an opening for routing catheters, tubes, wires, and other items to the legs of the patient.

FIG. 2 is an exploded view of the embodiment of the thermal blanket 10 illustrated in FIG. 1. The base sheet 204 is a substantially rectangular sheet fabricated of a substantially air permeable material, such as, for example, a natural or synthetic non-woven material through which air under pressure can be communicated. Whereas synthetic materials such as, for example, polyester, can be used, the use of a cellulose or paper based material has advantages where a single use, disposable thermal blanket 10 is desired. In another embodiment, the base sheet 204 is fabricated of an air impermeable material that is provided with openings through which gas can pass. In still another embodiment, the base sheet 204 is fabricated of a material that is air permeable in selected areas and otherwise air impermeable. The top sheet 202 is a substantially rectangular sheet fabricated out of a substantially air impermeable material, such as, for example, a cellulose based sheet material coated with a film of polyethylene or polypropylene. Between the base sheet 204 and the top sheet 202 is a barrier sheet 106, which is impervious to gas. The barrier sheet 106 is a substantially rectangular sheet fabricated out of an air impermeable material, such as, for example, polyethylene or polypropylene.

Reinforcing collar 212 for the inlet port 140 has an opening 214 for receiving the end of the supply hose from a blower. The collar 212 is secured to the top sheet 202 with an adhesive. The opening 214 is approximately 2¼ inches in diameter. In one embodiment, the top sheet 202 does not have a corresponding opening in the top sheet 202. When the thermal blanket 10 is used, the portion of the top sheet 202 within the opening 214 is torn to allow the insertion of the end of the hose. In another embodiment, the area to be torn is scored to aid in tearing.

The base sheet 204, the top sheet 202, and the barrier sheet 106 are heat bonded together within the inflated portion 114 of the blanket 10 at seams 122, 124, 132, 134, 136, 138. The base sheet 204 and the top sheet 202 are heat bonded together to form the inflated portion 114 of the blanket 10 at seam 112. The seams 112, 116, 122, 132, 134, 136, 138 are formed, in one embodiment, by heat bonding. Those skilled in the art will recognize that various adhesive or other bonding methods can be used without departing from the spirit or scope of the present invention.

In the illustrated embodiment, the barrier sheet 106 extends from the foot of the blanket 10 to the opening 104. In another embodiment, the barrier sheet 106 extends the full length of the blanket 10, with the portion covering the opening 104 cut out. Also illustrated in FIG. 2 is a barrier sheet 106' that is used with another embodiment instead of the shorter sheet 106. The long barrier sheet 106' extends the full length of the blanket 10, with an opening 104' coinciding with the opening 104 and with a cutout portion 102' coinciding with the neck slot 102. The illustrated embodiment shows the long barrier sheet 106' wider than the opening 104 however, if the barrier sheet 106' is no wider than the opening 104, then the barrier sheet 106' will be in two sections. Although FIG. 2 illustrates two barrier sheets 106, 106', it is intended that only one sheet 106, 106' be used for each embodiment.

In the illustrated embodiment, the opening 104 is shown as being formed in the base sheet 204 and the top sheet 202. In another embodiment, the sheets 202, 204 are joined before the opening 104 is formed in the blanket 10.

In one embodiment, the blanket 10 is sterilizable for use in a sterile environment. In one such embodiment, the blanket 10 is sterilizable by conventional sterilization techniques. The material of the sheets 202, 204 and 106 of blanket 10 is such that conventional sterilization techniques do not damage or degrade the material. It is understood by those skilled in the art, that once sterilized, the blanket 10 is placed in a protected container, package or carrier which prevents the blanket 10 from being contaminated.

FIG. 3 illustrates another embodiment of a therapy blanket 10' for covering a lower portion of a patient. In this embodiment, the inflatable portion 114' is sized to cover the lower portion of the patient. Sections of tape 302, 304, 306 are attached to an edge of the blanket 10' for attaching the blanket 10' to the patient. The sections of tape 302, 304, 306 prevent the exhausted air from blowing over the patient's chest or abdominal area.

The inflatable portion 114' of the illustrated embodiment is bounded by seams 112, 312, 314, 316. The conditioned air is exhausted in a pair of air flow channels 142', 144' located on the sides of the inflatable portion 114'. Between the channels 142', 144' are a group of parallel inside channels 152, 154 defined by seams 132, 134, 136. These channels 152, 154 serve to flatten the blanket 10' across the legs of the patient. Because of the barrier sheet 106, the conditioned air does not exhaust through the inside channels 152, 154.

Seams 312, 314 are double wide seams with perforations aligned along the centerline of the seams 312, 314. By pulling the fabric of the blanket 10' away from the seams 312, 314, the perforations separate and the un-inflated portion 322 separates from the blanket 10' at the seams 312, 314, thereby allowing access to an exposed portion of the patient either by folding the un-inflated portion 322 away from the patient or by securing the tape 304 to the patient and routing catheters, tubes, wires, an d other items to the patient through the slits opened at the seams 312, 314.

Various portions of the inflatable thermal blanket perform various functions. The function of forming an inflatable portion is implemented by the top sheet 202 and the base sheet 204 joined at seams 112, 116 to form an inflatable portion 114, 114' and seams 112, 116, 132, 134, 136 form a pair of outside channels 142, 144 and at least one channel 152, 154 formed between said pair of outside channels 142, 144.

The function of introducing the conditioned gas into the inflatable portion 114, 114' is performed by the inlet port 140. The function of exhausting the conditioned gas from the inflatable portion 114, 114' is implemented by the base sheet 204 being formed of an air permeable material. In one embodiment, the base sheet 204 is formed of a material that is air permeable. In another embodiment, the base sheet 204 is formed of a material with orifices that pass the conditioned air. In one embodiment, the function of exhausting the conditioned gas is implemented by the inflatable portion 114, 114' which includes a pair of outside channels 142, 144, 142', 144', which exhaust conditioned air through the air permeable base sheet 204. In another embodiment, the function of exhausting the conditioned gas is implemented by the inflatable portion 114, 114' which includes a pair of outside channels 142, 144, 142', 144', which exhaust conditioned air through the air permeable base sheet 204, and at least one inside channel 152, 154, and the inside channels 152, 154 include a barrier sheet 106 which prevents conditioned air from being exhausted from the inside channels 152, 154.

The function of providing access through the inflatable portion 114, 114' is performed by the access opening 104. The function of preventing the conditioned gas from being exhausted towards the access opening 104 in the inflatable portion 114, 114' is implemented by excess material between the edge of the access opening 104 and the seam 112 defining the opening 104. This excess material is adapted for taping to the body or other covering of the patient.

The function of preventing the conditioned gas from being immediately exhausted toward a patient is implemented, in one embodiment, by the barrier sheet 106. In another embodiment, the un-inflated regions defined by seams 122 redirect the conditioned gas and prevent the immediate exhaustion of the conditioned gas toward the patient.

The function of moderating a temperature of the conditioned gas in the inflatable portion 114, 114' is implemented by the channels 142, 144, 142', 144', 152, 154 formed in the inflatable portion, in combination with the barrier sheet 106. The temperature is moderated by preventing the air from being immediately exhausted toward the patient and routing the conditioned air through the various channels 142, 144, 152, 154 to allow mixing with cooler air in the inflatable portion 114, 114' and to allow the conditioned air to cool slightly as it travels through the channels 142, 144, 152, 154.

The function of restricting the conditioned gas from being exhausted from the at least one inner channel 152, 154 is implemented by the barrier sheet 106 being positioned in the area of the inner channels. The function of sterilizing the blanket 10, 10' is implemented by sterilizing the fully assembled blanket 10, 10' and enclosing it in a container to prevent contamination.

The function of providing a second access through the blanket 10, 10' is implemented, in one embodiment, by the perforated seam 138, which can be separated to form a slit. In another embodiment, the blanket 10, 10' has perforated seams 152, 154, which can be separated to form slits through which instruments and tubes can be routed to the patient. In other embodiments, the blanket 10' has perforated seams 312, 314, which can be separated to form, in one embodiment, a flap 322, which can be folded over, or, in another embodiment, slits through Which instruments and tubes can be routed to the patient.

The function of securing the blanket 10' to the patient is implemented by the tape sections 302, 304, 306 attached to the end of the blanket 10' that is positioned proximal the patient's torso. The function of creating a slit is implemented, in various embodiments, by perforating a seam 138, 152, 154, 312, 314.

From the foregoing description, it will be recognized by those skilled in the art that a pneumatic therapy blanket with sterile access has been provided. An inflatable therapy blanket has an opening in the patient's chest area. In another embodiment, perforated seams are positioned along the longitudinal axis of the blanket. By breaking the perforation, a slit is formed, allowing access to the patient's body from outside the blanket.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. An inflatable thermal blanket for providing a conditioned gas to a portion of a body of a human and providing access to the human, said inflatable thermal blanket comprising:
   a first sheet fabricated of an air permeable material;
   a barrier sheet that is impermeable to the conditioned gas; and
   a second sheet fabricated of an air impermeable material, said first sheet and said second sheet having a cutout portion adapted to fit about a neck of the human, said barrier sheet disposed between said first sheet and said second sheet said barrier sheet disposed adjacent to said first sheet, said second sheet attached to said first sheet at a first seam, said first seam defining an inflatable portion, said inflatable portion including:
      an inlet port opening into said inflatable portion, said inlet port for receiving the conditioned gas;
      a pair of outside channels positioned along opposing sides of the inflatable portion, said pair of outside channels for exhausting the conditioned air;
      at least one channel formed between said pair of outside channels, said barrier sheet positioned in said at least one channel for preventing the exhaustion of the conditioned air from said at least one channel; and
      an access opening positioned between said pair of outside channels, said access opening defined by a second seam joining said first sheet and said second sheet, said access opening penetrating said first sheet and said second sheet, said access opening having a lip between an edge and said second seam.

2. The inflatable thermal blanket of claim 1 wherein said inflatable thermal blanket is sterilizable.

3. The inflatable thermal blanket of claim 1 wherein said barrier sheet is a continuous sheet that is air impermeable, said barrier sheet having a cutout portion adapted to fit about a neck of the human.

4. The inflatable thermal blanket of claim 1 further including a perforated seam for creating a slit.

5. The inflatable thermal blanket of claim 4 wherein said perforated seam is located between a neck cutout portion and said through-opening.

6. The inflatable thermal blanket of claim 4 wherein said perforated seam is located between said pair of outside channels.

7. An inflatable thermal blanket for providing a conditioned gas to a portion of a body of a human and providing access to the human, said inflatable thermal blanket comprising:
   an inflatable portion formed from a first sheet and a second sheet, said first sheet being air permeable and said second sheet being air impermeable, said inflatable portion including:
      an inlet port opening into said inflatable portion, said inlet port for receiving the conditioned gas;
      a pair of outside channels positioned along opposing sides of the inflatable portion, said pair of outside channels for exhausting the conditioned air;
      at least one channel formed between said pair of outside channels;
      a barrier sheet positioned in said at least one channel for preventing the exhaustion of the conditioned air from a portion of said inflatable portion said barrier sheet disposed adjacent to said first sheet; and
      an access opening positioned between said pair of outside channels, said through-opening defined by a second seam joining said first sheet to said second sheet, said access opening penetrating said first sheet and said second sheet, said access opening having a lip between an edge and said second seam.

8. The inflatable thermal blanket of claim 7 further including a cutout portion adapted to fit about a neck of the human.

9. The inflatable thermal blanket of claim 7 wherein said barrier sheet is a continuous sheet that is air impermeable.

10. The inflatable thermal blanket of claim 7 further including a perforated seam located between a neck cutout portion and said through-opening, said perforated seam for creating a slit.

11. The inflatable thermal blanket of claim 7 further including a perforated seam located between said pair of outside channels, said perforated seam for creating a slit.

12. The inflatable thermal blanket of claim 7 wherein said inflatable thermal blanket is sterilizable.

13. An inflatable thermal blanket for providing a conditioned gas to a portion of a body of a human and providing access to the human, said inflatable thermal blanket comprising:
   an inflatable portion formed from a first sheet and a second sheet, said first sheet being air permeable and said second sheet being air impermeable, said inflatable portion including:
      an inlet port opening into said inflatable portion, said inlet port for receiving the conditioned gas;
      a pair of outside channels positioned along opposing sides of the inflatable portion, said pair of outside channels for exhausting the conditioned air;
      at least one channel formed between said pair of outside channels; and
      a barrier sheet positioned in said at least one channel for preventing the exhaustion of the conditioned air from said at least one channel said barrier sheet disposed adjacent to said first sheet; and
      at least one tape strip attached to an edge of said inflatable thermal blanket, said at least one tape strip adapted for securing said inflatable thermal blanket to the human.

14. The inflatable thermal blanket of claim 13 wherein said inflatable thermal blanket is sterilizable.

15. The inflatable thermal blanket of claim 13 further including a perforated seam located between said pair of outside channels, said perforated seam for creating a slit.

16. An inflatable thermal blanket for providing a conditioned gas to a portion of a body of a human and providing access to the human, said inflatable thermal blanket comprising:

a means for forming an inflatable portion;

a means for introducing the conditioned gas into said inflatable portion;

a means for exhausting the conditioned gas from said inflatable portion;

a means for providing access through said inflatable portion; and a means for preventing the conditioned gas from being immediately exhausted toward a patient.

17. The inflatable thermal blanket of claim 16 further including a means for preventing the conditioned gas from being exhausted towards an access opening in said inflatable portion.

18. The inflatable thermal blanket of claim 16 further including a means for providing a second access through said inflatable thermal blanket.

19. An inflatable thermal blanket for providing a conditioned gas to a portion of a body of a human and providing access to the human, said inflatable thermal blanket comprising:

a means for forming an inflatable portion;

a means for introducing the conditioned gas into said inflatable portion;

a means for exhausting the conditioned gas from said inflatable portion;

a means for providing access through said inflatable portion; and a means for moderating a temperature of the conditioned gas in said inflatable portion.

* * * * *